(12) United States Patent
Brabec et al.

(10) Patent No.: US 7,844,347 B2
(45) Date of Patent: Nov. 30, 2010

(54) MEDICAL DEVICES INCORPORATING CARBON NANOTUBE MATERIAL AND METHODS OF FABRICATING SAME

(75) Inventors: Scott J. Brabec, Elk River, MN (US); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1175 days.

(21) Appl. No.: 10/403,329

(22) Filed: Mar. 31, 2003

(65) Prior Publication Data

US 2004/0111141 A1 Jun. 10, 2004

Related U.S. Application Data

(60) Provisional application No. 60/431,330, filed on Dec. 6, 2002.

(51) Int. Cl.
*A61N 1/04* (2006.01)
(52) U.S. Cl. ........................ 607/121; 607/115; 600/372; 600/395
(58) Field of Classification Search ......... 607/115–119, 607/121–122, 120; 600/372–374, 377, 395, 600/595
See application file for complete search history.

(56) References Cited

U.S. PATENT DOCUMENTS

| | | | |
|---|---|---|---|
| 4,649,937 A | | 3/1987 | DeHaan et al. |
| 4,679,572 A | | 7/1987 | Baker, Jr. |
| 5,074,313 A | | 12/1991 | Dahl et al. |
| 5,097,543 A | | 3/1992 | Oille |
| 5,097,843 A | | 3/1992 | Soukup et al. |
| 5,324,325 A | * | 6/1994 | Moaddeb .................... 607/120 |
| 5,326,448 A | | 7/1994 | Otten |
| 5,431,649 A | * | 7/1995 | Mulier et al. ................. 606/41 |
| 5,571,158 A | | 11/1996 | Bolz et al. |
| 5,609,622 A | * | 3/1997 | Soukup et al. .............. 607/122 |
| 5,639,276 A | * | 6/1997 | Weinstock et al. .......... 606/129 |
| 6,031,711 A | | 2/2000 | Tennent et al. |
| 6,099,524 A | * | 8/2000 | Lipson et al. ................. 606/41 |
| 6,240,320 B1 | | 5/2001 | Spehr et al. |
| 6,265,466 B1 | * | 7/2001 | Glatkowski et al. ......... 523/137 |
| 6,273,875 B1 | | 8/2001 | Siman et al. |

(Continued)

FOREIGN PATENT DOCUMENTS

EP 0057877 A1 8/1982

(Continued)

OTHER PUBLICATIONS

Sloan, J., et al., "Two Layer 4:4 Co-coordinated KI Crystals Grown Within Single Walled Carbon Nanotubes", *Elsevier, Chemical Physics Letter*, 329 (2002) 61-65.

(Continued)

*Primary Examiner*—Carl H Layno
*Assistant Examiner*—Natasha N Patel

(57) ABSTRACT

Unique electrodes and/or electrical lead assemblies are provided for stimulating cardiac tissue, muscle tissue, neurological tissue, brain tissue and/or organ tissue; to electrophysiology mapping and ablation catheters for monitoring and selectively altering physiologic conduction pathways. The electrodes, lead assemblies and catheters optionally include fluid irrigation conduit(s) for providing therapeutic and/or performance enhancing materials to adjacent biological tissue. Each device is coupled to or incorporates nanotube structures or materials therein. Methods for fabricating, deploying, and operating such medical devices are also provided.

34 Claims, 5 Drawing Sheets

U.S. PATENT DOCUMENTS

| | | | |
|---|---|---|---|
| 6,280,697 | B1 | 8/2001 | Zhou et al. |
| 6,311,088 | B1 | 10/2001 | Betzold et al. |
| 6,361,861 | B2 | 3/2002 | Gao et al. |
| 6,434,430 | B2* | 8/2002 | Borgersen et al. ............ 607/122 |
| 6,576,341 | B1* | 6/2003 | Davey et al. ................ 428/376 |
| 6,743,463 | B2* | 6/2004 | Weber et al. ............... 427/2.24 |
| 6,999,821 | B2* | 2/2006 | Jenney et al. ............... 607/122 |
| 2003/0077515 | A1* | 4/2003 | Chen et al. ............... 429/231.8 |
| 2004/0064174 | A1* | 4/2004 | Belden ....................... 607/122 |
| 2005/0075708 | A1* | 4/2005 | O'Brien et al. ............. 607/116 |

FOREIGN PATENT DOCUMENTS

EP  0451498 B1  10/1991

OTHER PUBLICATIONS

Sloan, Eric, "Pulling Nanotubes Makes Thread", *TRN the Latest Technolgy Research News*, Oct. 30/Nov. 6, 2002.

McEuen, Paul L., "Single-Walled Carbon Nanotube Electronics", *IEEE Transactions on Nanotechnology*, 2002.

Rodriguez, N.M., "Catalytic Engineering of Carbon Nanostructures", *Langmuir*, 1995.

Mirsky, Steve, "Tantalizing Tubes", Scientific_American.com, Jun. 20, 2002.

Yarris, Lynn, "Atom-Sized Electronic Devices Identified Within Carbon Nanotubes", Berkley Lab Research News, Dec. 15, 1997.

Schewe, P. et al., "A Carbon Nanotube Integrated Circuit", Physics News 531, Mar. 22, 2001.

Li, W. et al. "Large-Scale Synthesis of Aligned Carbon Nanotubes", Science, vol. 274, Issue 5293, 1701-1703, Dec. 6, 1996.

Beierlein, "Functionalization of Carbon Nanotubes for the Self-Assembly of Hybrid Structures", Department of Physics and Center for NanoScience, Ludwig-Maximilians University, Munich, Germany, Feb. 17, 2005. Retrieved on Apr. 12, 2010 from the Internet:<URL: http://nano.tu-dresden.de/pubs/slides_others/2005_02_17_udo_beierlein.pdf>; 21 pgs.

Chen et al., "Noncovalent Functionalization of Carbon Nanotubes for Highly Specific Electronic Biosensors", *PNAS*, Apr. 29, 2003; 100(9):4984-4989.

Gulseren, "Functionalization of Carbon Nanotubes Deformations, Reconstructions and Device Applications: A First-Principles Study", Department of Physics, Bilkent University, Ankara, Turkey, Apr. 25, 2005. Retrieved on Apr. 12, 2010 from the Internet:<URL: http://cdsagenda5.ictp.trieste.it/html_trees_links/1590597488/Gulseren/Funct_Carbon_%20Nanotubes_Def.pdf>; 20 pgs.

Singh et al., "Covalent Functionalization of Single Walled Carbon Nanotubes with Peptide Nucleic Acid: Nanocomponents for Molecular Level Electronics", *Carbon*, 2006; 44:1730-1739.

* cited by examiner

MEDICAL DEVICES INCORPORATING CARBON NANOTUBE MATERIAL AND METHODS OF FABRICATING SAME

CROSS REFERENCE TO RELATED APPLICATIONS

This non-provisional patent application hereby claims the benefit of provisional U.S. patent application Ser. No. 60/431,330 filed 6 Dec. 2002 and entitled, "Medical Devices Incorporating Carbon Nanotube Material and Methods of Fabricating Same," the entire contents of which are hereby incorporated by reference as if fully set forth herein.

This non-provisional patent application also incorporates the contents of co-pending non-provisional U.S. patent application Ser. No. 10/262,046 filed 2 Oct. 2002 and entitled, "Active Fluid Delivery Catheter."

FIELD OF THE INVENTION

The present invention relates generally to medical devices; in particular and without limitation, to unique electrodes and/or electrical lead assemblies for stimulating cardiac tissue, muscle tissue, neurological tissue, brain tissue and/or organ tissue; to electrophysiology mapping and ablation catheters for monitoring and selectively altering physiologic conduction pathways; and, wherein said electrodes, lead assemblies and catheters optionally include fluid irrigation conduit(s) for providing therapeutic and/or performance enhancing materials to adjacent biological tissue, and wherein each said device is coupled to or incorporates nanotube structures or materials therein. The present invention also provides methods for fabricating, deploying, and operating such medical devices. For the uninitiated, to get an idea of scale—one nanometer is one one-thousandth of a micrometer; in comparison, a strand of human hair is typically 50 to 100 micrometers thick.

BACKGROUND OF THE INVENTION

Even brief study of the prior art relating to medical electrical leads will reveal that such leads typically incorporate at least one electrode and the lead assembly should be compact and resilient, should yield a low threshold for stimulation, should sense the low amplitude electrical signals naturally generated by a body. In addition, such leads should be biocompatible with the adjacent body tissue and body fluids, which it contacts. Various attempts have been made to improve these characteristics, especially with respect to medical electrodes electrically coupled to the lead body of a cardiac pacing lead. Generally these attempts are aimed at increasing the interfacial, or active, surface area of an electrode by the use of surface treatments or coatings that are considered highly biocompatible.

As is known in the art, electrochemical reactions occur at the electrode-tissue interface when an electrical stimulation pulse is delivered through a medical electrical lead assembly. This phenomenon is referred to as "polarization," which is known to interfere with efficient delivery of the stimulation pulses. High interfacial impedance due to the effects of polarization reduces the effective charge transfer of the stimulation pulse to the targeted tissue. Therefore low polarization electrodes have been developed to reduce this effect and improve the transfer of charge from the electrode to the tissue.

One method for reducing polarization effects is to increase electrode surface area. However, a design trade-off exists in increasing the electrode size since medical leads and the electrodes they carry are preferably of small dimensions such that they may be easily implanted. For example, presently available cardiac pacing leads typically have cross-sectional diameters of greater than about three or four French and a typical diameter of an electrophysiology catheter is about six French. For reference, a single French unit of measurement equals one third of a millimeter. In any event, to overcome this trade-off, methods for increasing the active surface area of a geometrically down-sized electrode have been proposed. For example, treatments or coatings that yield a porous, irregular or grooved surface increase the active surface area of the electrode and thereby diminish the effects of polarization. Various coatings have been proposed and put into commercial use for producing low polarization electrodes such as platinum black, pyrolytic carbon, iridium oxide, vitreous carbon, titanium nitride and others.

A further benefit of increasing electrode interfacial or active surface area can be improved electrode sensing performance. Cardiac signals, including action potentials that are relatively low amplitude, monophasic signals, may be more readily sensed when the active surface area of the electrode is increased. Moreover, an evoked response following delivery of a stimulation pulse may be more readily detected when post-pace polarization artifact is diminished.

Recently, as reported in the Journal of the American Chemical Society (JACS), research personnel at Washington University in St. Louis and their collaborators report that they have made boron "nanowhiskers" by chemical vapor deposition. The particles have diameters in the range of 20 to 200 nanometers and the whiskers (also called nanowires) are semiconducting and show properties of elemental boron.

The group at Washington University in St. Louis turned to boron, one spot to the left of carbon in the periodic table, to see if it would be a good candidate. They postulated that if nanotubes could be made of boron and produced in large quantities, they should have the advantage of having consistent properties despite individual variation in diameter and wall structure. The discovery that the "nanowhiskers" are semiconducting make them promising candidates for nanoscale electronic wires. Boron nitride nanotubes, which are similar in structure to carbon nanotubes, are electrically insulating. Boron nanotubes on the other hand may be grown into long thin wire-like structures. At first they appeared hollow, but after closer examination, they were determined to be dense whisker-like structures, not hollow nanotube structures. The notion of boron nanotubes creates more excitement in nanotechnology than nanowhiskers because of their unique structure, which could be likened to a distinct form of an element. Carbon, for instance, is present as graphite and diamond, and, recently discovered, in "buckyball" and nanotube conformations. Also, boron nanotubes are predicted by theory to have very high conductivity especially when bulk boron is "doped" with other atoms to increase conductivity. Carbon nanotubes also have been doped, as have various other kinds of nanowires, and assembled in combinations of conducting and semiconducting ones to make for several different microscale electronic components such as rectifiers, field-effect transistors and diodes.

SUMMARY OF THE INVENTION

The present invention is directed at providing a class of improved medical electrical lead assemblies featuring carbon nanotube material. Carbon nanotubes, discovered in about 1991, are formed from a cage-like hollow lattice structure of carbon molecules arranged into tubes having a diameter on the order of nanometers. Considerable interest in the use of carbon nanotubes in various applications such as batteries, capacitors, flat panel displays and microelectronics, has grown due to the unique properties of this newly discovered material including its high strength, stable state, low weight, and so-called ballistic (or near-superconducting) electrical properties. In addition, boron nanotubes and carbon nanotube "nanowires" are now becoming available. The inventors have discovered that these developments enable invention of discrete technologies providing significant value to patients suffering from diverse afflictions while advancing the medical device field in several important ways.

Nanotubes made exclusively from carbon are chemically inert and are therefore, the inventors suggest, highly biocompatible. Carbon nanotubes may be formed to have metallic conductor or semi-conductor properties and are capable of sustaining a high current density, on the order of hundreds of times greater than common metals. Carbon nanotubes are thin, long tubular macromolecules with diameters on the order of a 1-200 nanometers (molecules are on the order of a few nanometers) and with lengths on the order of micrometers to millimeters. Bundles of such nanotubes create nanostructures which are characterized by a large surface area. In short, these characteristics of carbon nanotubes may make them particularly well-suited for diverse uses in conjunction with medical electrical lead assemblies and medical electrodes for improving electrode performance.

The inventors have discovered that carbon nanotubes may be adapted to render greatly improved medical electrical leads and/or medical electrodes. The present invention provides such leads and/or electrodes in one or more of the following ways. Nanotube structures are coupled to, layered upon or coated upon an electrically conductive or non-conductive electrode or lead body structure. In addition, a variety of polymers and other resin-based materials when combined, encapsulated or impregnated with nanotubes can be used to render the resulting structures electrically conductive. In the context of the present invention, such structures may be configured as elongated medical lead body structures, electrode structures and the like. In addition, carbon nanotubes may be employed in lieu of a metallic coil conductor (or other type) of primary electrical conductor for all or a portion of the body of an extremely thin, resilient and flexible medical electrical lead. The resulting structure may be porous and itself impregnated with diverse materials such as steroid material, electrically conductive fluid or paste materials, and the like.

One embodiment of the present invention features a medical electrical lead carrying one or more tip-, ring-, defibrillation coil-, neurological-, brain-, skeletal muscle-, or organ- electrodes for sensing and/or delivering electrical stimulation pulses to a portion of cardiac tissue, neurological tissue, brain tissue, skeletal tissue, organ tissue and the like.

In embodiments involving cardiac tissue, the active surface area of the electrodes, which is in contact with blood or bodily tissue, is increased by depositing carbon nanotubes on the electrode surface. Furthermore, carbon nanotubes at the electrode/tissue interface emit electrons from the tip portions of the nanotubes at relatively low voltages and sustain current densities hundreds of times greater than common metals. Such field emission properties can be obtained by mixing nanotubes into a composite paste with polymers such as polyurethane or silicone, applying the paste to an electrode surface, and then applying a voltage to align the nanotubes on end. Such alignment can form extremely consistent, tightly packed arrays of nanotubes or may be less consistent. In either case, a vast surface area is created which is very advantageous as is known to those of skill in the art. Such arrays of nanotubes may be impregnated with diverse materials such as biological, genetic or pharmacological substances so that over time said arrays elute the materials into adjacent tissue or body fluid. Some representative diverse materials include steroid material, electrically conductive fluid materials such as isotonic saline solution or other biologically compatible fluids.

In another embodiment, a carbon nanotube coating may be applied to a metallic electrode substrate, such as platinum, platinum-iridium, titanium, alloys of the foregoing and other metals by chemical vapor deposition or other methods known in the art for growing and depositing carbon nanotubes on a substrate. The surface area of the carbon nanotubes, which may include the outer surface and the inner surface of the tubes, effectively increases the active electrode surface area of the metallic electrode substrate.

The carbon nanotube coating provides a highly biocompatible electrode surface. Moreover, the carbon nanotube coating provides a low electrode-tissue interface impedance allowing for improved sensing of low frequency, intrinsic cardiac signals as well as evoked responses from cardiac tissue. The high-energy density properties of carbon nanotubes further provides lower stimulation thresholds for capturing a heart during pacing and/or when delivering defibrillation therapy to a heart.

While chemical vapor deposition (CVD) represents one manner of mass producing apparatus according to the present invention, CVD generally has a higher density of structural defects and a subsequently a larger variation in resistivity. Metallic catalysts such as nickel, iron, cobalt, molybdenum and ruthenium are usually necessary for formation of consistent, high yield films using CVD. Achieving good contact resistances to the substrate material is still a matter of adapting the catalyst and substrate to one another, among other variables. If the formation of thin oxide layers, on the atomic scale, occur between the nanotubes and metal substrate, high ohmic-contact resistance is often the result. As research continues with respect to high yield, mass production of carbon nanotube coatings, there are now presently available highly ordered single-wall and multi-wall nanotube structures on substrates in a very ordered manner.

In this patent disclosure the term "nanotube(s)" is intended to refer to nanostructures in general; that is, substantially one dimensional so-called nanowires (or "nanowhiskers"), two dimensional, substantially planar structures such as fullerenes (e.g., a convex cage of atoms with only hexagonal and/or pentagonal faces) having a cylindrical shape, and three-dimensional structures such as the so-called buckyballs, closed- and open-ended nanotubes, and the like. The inventors suggest that when incorporated into suitably adapted structures the fully variety of nanostructures may be used to improve the electrical performance of myriad medical electrical leads. In some applications, the nanostructures may also be used to retain and/or release over time the above-noted diverse materials, such as electrically conductive fluids, biological, genetic and/or pharmacological substances. Thus, the terms used in the present patent disclosure may differ from the evolving convention(s) for referring to a broad variety of different nano-scale structures. For example, typically, a nanotube is any tube having nanoscale dimensions, but is often intended to generally refer to carbon nanotubes. In this disclosure the reverse is true. Thus, in this disclosure "nanotube" or "nanostructure" is intended to include carbon nanotubes and other nanostructures, and shall also be deemed to cover a often mentioned non-carbon variety of nanotube made of boron and the like. In general, then, nanotubes are sheets of graphite rolled up to make a tube. The dimensions are variable (down to 0.4 nm in diameter) and a single nanotube can be formed or disposed within another nanotube, leading to a distinction between multi-walled and single-walled nanotubes ("MWNT" and "SWNT," respectively).

Apart from remarkable tensile strength, nanotubes exhibit varying electrical properties (depending on the way the graphite structure spirals around the tube, and other factors), and can be insulating, semiconducting or conducting (metallic).

Nanotubes can be either electrically conductive or semiconductive, depending on their helicity, leading to nanoscale wires and electrical components. These one-dimensional fibers exhibit electrical conductivity as high as copper, thermal conductivity as high as diamond, strength 100 times greater than steel at one sixth the weight, and high strain to failure.

Carbon nanotubes exhibit extraordinary mechanical properties: the Young's modulus is over 1 Tera Pascal and as stiff as diamond with an estimated tensile strength of about 200 Giga Pascal. These properties are ideal for reinforced composites and nanoelectromechanical systems, among others.

Carbon nanotube transistors exploit the fact that nm-scale nanotubes are ready-made molecular wires and can be rendered into a conducting, semiconducting, or insulating state, which make them valuable for future nanocomputer design. Carbon nanotubes are quite popular now for their prospective electrical, thermal, and even selective-chemistry applications.

While the present invention will be described primarily with reference to single- and multi-walled carbon nanotubes (SWNT/MWNT), it is not to be construed as being limited solely to such materials. For example, the present invention may be practiced using so-called "nanowires" or "nanowhiskers" (NW). Such NW may be produced of carbon or other related elements such as boron and the NW (and SWNT/MWNT) may be doped or modified so they readily conduct electricity, are semi-conductive, or even insulative.

The foregoing summary is intended to briefly introduce the reader to the basic concepts of the present invention and should not be construed as limiting the invention hereof. Likewise, the following drawings (and those incorporated herein) are illustrative of only a few embodiments of the present invention, are not drawn to scale and should not be viewed as limiting the scope of the present invention. In fact, those of skill in the art will quickly recognize variations of the described and depicted embodiments of the present invention, and each such variation is intended to be covered by this patent disclosure.

DETAILED DESCRIPTION OF THE INVENTION

Figure 1A:
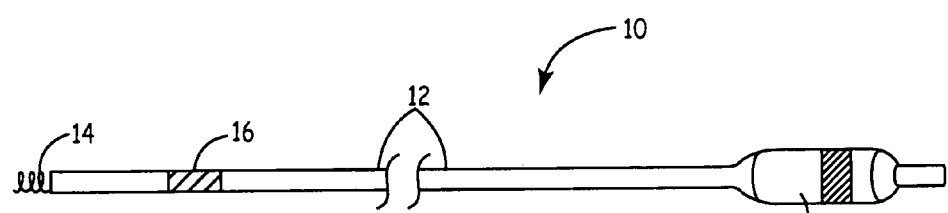
FIG. 1A is a plan view of a cardiac pacing lead that may be used in conjunction with the present invention. It should be noted that the pacing lead may have one or more anode rings.
Figure 1B:
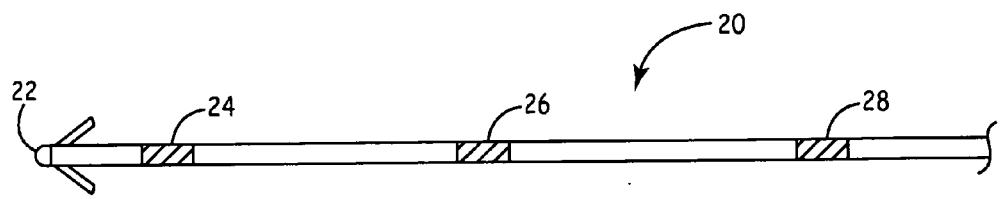
FIG. 1B is a plan view of the distal end of a cardiac pacing and defibrillation lead that may be used in conjunction with the present invention.

As described above, the present invention is directed at providing a medical lead having improved electrode performance by providing carbon nanotube coated electrodes. FIGS. 1A and 1B depict exemplary medical leads of the type that may be used with the present invention. FIG. 1A is a plan view of a medical lead 10 that may typically be used for cardiac pacing and/or sensing. Lead 10 is provided with an elongated lead body 12, a helical tip electrode 14 located at the distal end of the lead and a ring electrode 16 spaced proximally from tip electrode 14. A connector assembly 18 at the proximal end of lead 10 is used to connect the lead to a medical device, such as a pacemaker. Conductors extending the length of lead body 12 electrically couple the tip electrode 14 and ring electrode 16 to respective connectors carried by the connector assembly 18.

FIG. 1B is a plan view of the distal end of a medical lead 20 of the type that may be used for pacing, sensing, cardioversion and/or defibrillation. Lead 20 is provided with a tip electrode 22 and a ring electrode 24, which are generally used for pacing and/or sensing, and two defibrillation coil electrodes 26 and 28 for delivering high-energy shocking pulses for cardioversion or, defibrillation.

The exemplary leads 10 and 20 of FIGS. 1A and 1B are shown to illustrate the various types of electrodes, including ring electrodes (16 and 24), coil electrodes (26 and 28), helical electrodes (14), or generally hemispherical electrodes (22), with which the present invention may be used. Other electrodes of various geometries may exist that may also benefit from the use of carbon nanotube coating as provided by the present invention. The application of the present invention is therefore not limited to the types of electrodes depicted in FIGS. 1A and 1B. The present invention may also be used in conjunction with electrodes for neurological stimulation or sensing, smooth or skeletal muscle sensing or stimulation or any other types of medical electrodes that may benefit from increased active surface area and/or increased current density capacity.

An electrode used with the present invention is preferably fabricated from a conductive biocompatible material appropriate for depositing carbon nanotubes thereto. CVD methods begin with supported catalyst particles that are exposed to a carbon feedstock gas (e.g., acetylene or methane). Carbon atoms from the dissociation of these molecules at the catalyst surface dissolve in the catalyst particles to reappear on the surface, where they organize to form nanotubes. Depending on the growth conditions (e.g. gas mixture, gas flows, reaction temperature, reaction time, and catalyst), the catalyst particle either remains on the surface (base growth) or is lifted from the surface by the nanotube (tip growth).

As mentioned earlier, adapting the catalyst to the substrate is critically important and note that catalysts can also be deposited to the substrate surface before introducing the carbon nanotubes. Noble metal substrates such as gold are known to suppress growth. The problem is most likely due to alloy formation with the catalyst material. Refractory metals and their nitrides can act as a diffusion barrier to the chosen catalyst. Also, applying an AC or DC electric field helps in nanotube growth.

The electrode material may be, for example, platinum, platinum-iridium, iridium, titanium or alloys, tantalum, and other non-noble metals. The electrode surface may also be treated or coated to enhance the surface for nanotube deposition, as will be further described below.

Carbon nanotubes may be grown and deposited onto a surface by at least three methods: 1) chemical vapor deposition, 2) carbon arc deposition, and 3) laser evaporation deposition. Chemical vapor deposition methods generally use a metal catalyst substrate at a high temperature to which a hydrocarbon gas is exposed. Carbon nanotubes are deposited on the catalyst surface and may be grown in various structures such as straight tubes that may be well-aligned or coiled tubes. A method for growing densely packed, uniform nanotube arrays perpendicular to a substrate is generally disclosed in U.S. Pat. No. 6,361,861 issued to Gao et al., incorporated herein by reference in its entirety.

Carbon arc deposition methods include evaporating material from a graphite electrode in an electric arc discharge between two graphite electrodes. Carbon nanotubes deposit on the other graphite electrode and are generally straight but may be impure with a high percentage of nanoparticles. Laser evaporation techniques involve forming carbon nanotubes in a plume of carbon vapor evaporated from a graphite target by a laser at high temperature.

Methods for growing and depositing carbon nanotubes on a substrate may produce varying purity, density, alignment, structure, and size of the nanotubes. Carbon nanotubes are formed as one or more concentric shells of graphite and therefore may be single-walled, double-walled or multi-walled tubes. Nanotubes may be straight or may have irregular curving or coiling shapes. Nanotubes reportedly range in diameter from 1 nanometer to several hundred nanometers. Nanotubes may be grown to be on the order of 1 micron to several hundred microns in length. Future methods for carbon nanotube growth and deposition may be developed that improve the purity, increase uniformity or achieve desired geometries or properties of the nanotubes, such as desired electrical properties.

Figure 2:
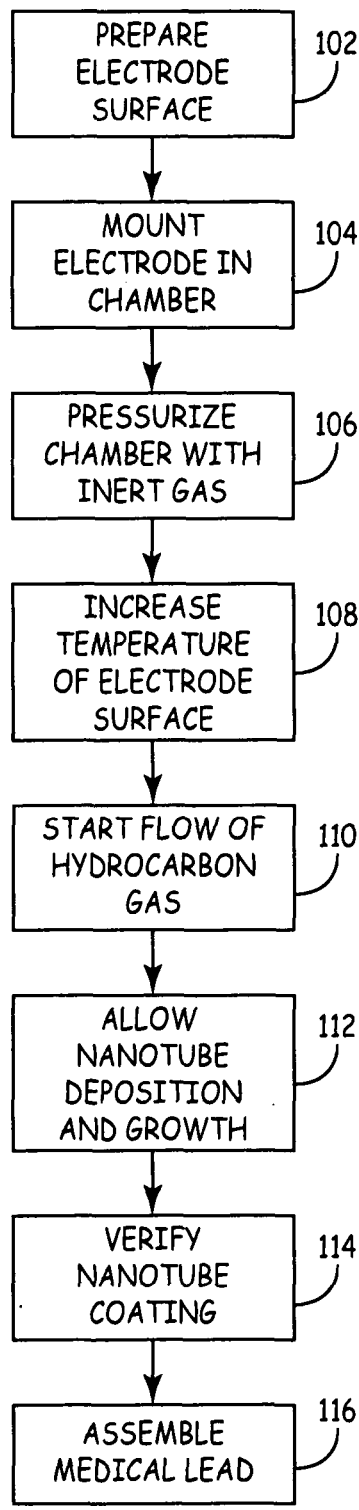
FIG. 2 is a flow diagram summarizing a method for manufacturing a carbon nanotube coated medical electrode.

In the present state of the art, carbon nanotube coated electrodes are contemplated to be produced by chemical vapor deposition methods, though any of the above described methods or modifications thereof or newly developed methods may be used. FIG. 2 is a flow chart depicting one method for producing a carbon nanotube coated electrode. The method may begin by preparing an electrode surface for deposition of the carbon nanotubes at step 102. The electrode is preferably fabricated from platinum or platinum-iridium. The electrode may take the form of any known types of electrodes, such as those shown in FIGS. 1A and 1B. The platinum iridium surface of the electrode may be a sufficient catalyst for carbon deposition. Alternatively, the electrode surface may be prepared by creating a more porous surface and/or coating the surface with an alternative biocompatible catalyst to promote strong bonding of the carbon nanotubes to the electrode surface or to enhance the deposition process. For example, a platinum electrode may be coated with a porous coating of catalytic nanoparticles. The porous coating may provide a better catalyst for carbon nanotube deposition in that the growth direction, size, and density of the nanotubes may be controlled by the pores (see Li et al., Science, 1996; 274(5239):1701-3.

The electrode may then be mounted in a vacuum chamber at step 104 through which an inert gas flows, such as a helium-argon gas, to raise the pressure in the chamber at step 106. The temperature of the substrate is raised at step 108. The temperature may typically be raised to a level on the order of 500 to 1000 degrees C. Resistive heating elements may be used to heat the substrate, although other equivalent means may be employed.

A carbon source in the form of a hydrocarbon gas, which may be, for example, acetylene gas, methylene gas, or ethylene gas, is then allowed to flow through the chamber at step 110. At step 112, nanotube deposition and growth are allowed to occur. The time required for adequately coating the electrode surface with a carbon nanotube coating may range from several minutes to several hours. The size of the nanotubes and their uniformity and density may be controlled by the flow rate of the hydrocarbon gas, the temperature of the substrate, the density of the catalyst on the substrate or other conditions.

Verification of the carbon nanotube coating may be performed by scanning electron microscopy or other methods at step 114. Verification may be performed to ensure a desired density or size of the nanotubes has been achieved or to ensure that the nanotubes are well attached to the electrode surface. The carbon nanotube coated electrode may then be assembled onto a lead at step 116 and electrically coupled to a conductor extending through the lead body.

Figure 3:
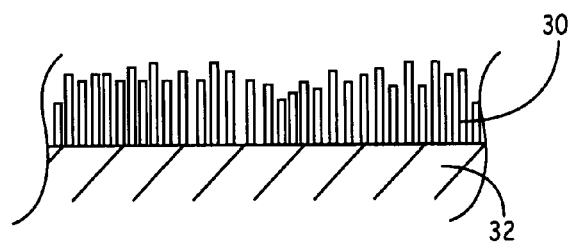
FIG. 3 is an illustration of a magnified, side view of a carbon nanotube coated electrode wherein the nanotubes are aligned.

Nanotubes may be deposited in an orderly, aligned fashion using various deposition methods. FIG. 3 is an illustration of a side view of an ordered nanotube "forest" 30 as it may be deposited on the surface of an electrode 32. The nanotube "forest" 30 may be grown such that the nanotubes are well aligned with one another and each generally have one end attached to the electrode surface. The nanotubes may be on the order of 0.1 to 300 microns in length and one to 200 nanometers in diameter depending on the deposition method used. A preferred range of diameters is in the range of approximately about one nm to about 20 nm but the present invention is not to be strictly limited to this range. In certain embodiments of the present invention a highly ordered array of SWNT members disposed approximately perpendicular to a supporting member having a diameter dimension on the order of approximately about one to about five nm diameters. But that does not mean an excellent electrode couldn't be had with random MWNT's about 200 nm diameter in a urethane paste and the like.

Figure 4:
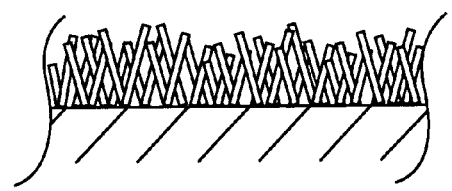
FIG. 4 is an illustration of a magnified, side view of a carbon nanotube coated electrode wherein the nanotubes are randomly ordered.

FIG. 4 illustrates an alternative arrangement of deposited nanotubes on a medical electrode surface. Nanotubes 36 may be deposited in a disorderly fashion wherein nanotubes 36 are straight but not aligned with respect to each other. The tubes will still have one end generally attached to the electrode surface 38.

Figure 5:
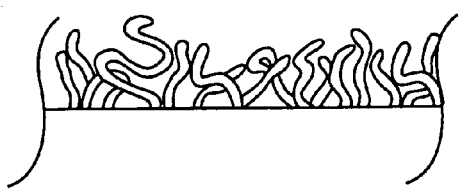
FIG. 5 is an illustration of a magnified, side view of a carbon nanotube coated electrode wherein the nanotubes are coiled and randomly arranged.

FIG. 5 illustrates yet another arrangement of deposited nanotubes 40 on a medical electrode surface 42. In this embodiment, coiled nanotubes 40, having one end attached to the electrode surface 42, are arranged randomly on electrode surface 42. Deposition methods resulting in coiled nanotubes have been described previously in the prior art.

The paste method described earlier is a preferred manner of coupling nanostructures to chronically implanted medical devices. In an alternative embodiment, carbon nanotubes may be grown and purified in a first process and then deposited onto an electrode surface as a coating in a second process. A method for depositing a purified carbon nanotube material onto a conductive substrate is generally disclosed in U.S. Pat. No. 6,280,697 issued to Zhou et al., incorporated herein by reference in its entirety.

Figure 6:
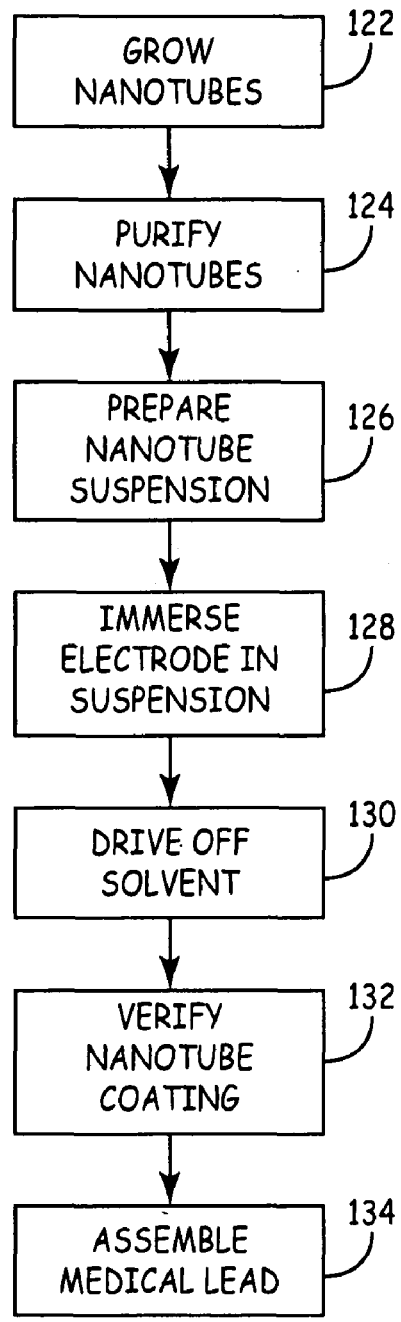
FIG. 6 is a flow chart summarizing an alternative method for manufacturing a carbon nanotube coated medical electrode.

FIG. 6 is a flow chart summarizing this alternative method for manufacturing carbon nanotube coated electrodes. Carbon nanotubes are grown at step 122 and purified at step 124. For example, carbon nanotubes may be formed by arc or laser deposition methods, or any known method, and purified by an appropriate method such as filtering through a microporous membrane. Alternatively, carbon nanotube materials that may be suitable for coating medical electrodes may be obtained directly from commercial sources such as NanoLab, Brighton, Mass.; CarboLex, Lexington, Ky.; Materials and Electrochemical Research Corporation, Tucson, Ariz., among a growing number of other suppliers.

At step 126, the nanotubes are suspended in a solvent, such as alcohol. An electrode to be coated may then be placed in a vessel with the suspension of carbon nanotubes at step 128. The solvent is then driven off at step 130 leaving a coating of nanotubes on the surface of the electrode. The nanotube coating may be verified at step 132 as described above. The electrode may then be assembled onto a medical lead at step 134.

The increase in active surface area created by a carbon nanotube coating is expected to be a minimum of 1,000× to potentially on the order of about 10,000×. This increase is theorized to result in a reduction in interfacial impedance at low frequencies from approximately 1000×, associated with prior known electrode coating methods such as sputtered porous titanium nitride, and iridium oxide. That is, the increase in active surface area created by a carbon nanotube coating is expected to be on the order off 1,000 to about 10,000×. The low frequencies referred to hereinabove, are on the order of less than about 0.1 Hz (or lower). Such a decrease in interfacial impedance improves electrode sensing performance which is very important for certain medical applications, such as cardiac rhythm management. This reduction in interfacial impedance and the high current density properties of carbon nanotubes also reduces pacing and/or defibrillation thresholds.

Methods for increasing the defects in the walls of the deposited nanotubes or for opening the ends of the tubes may be used to further increase the active surface area of the electrode. For example mechanical ball-milling or exposure to ultrasonic energy as generally disclosed in U.S. Pat. No. 6,280,697 may be applied to increase the available, accessible surface area. Theoretically, by creating more openings in the nanotubes, electrolytes may enter the tubes, which would expectedly further reduce the interfacial impedance, improving the electrode performance.

Figure 7:
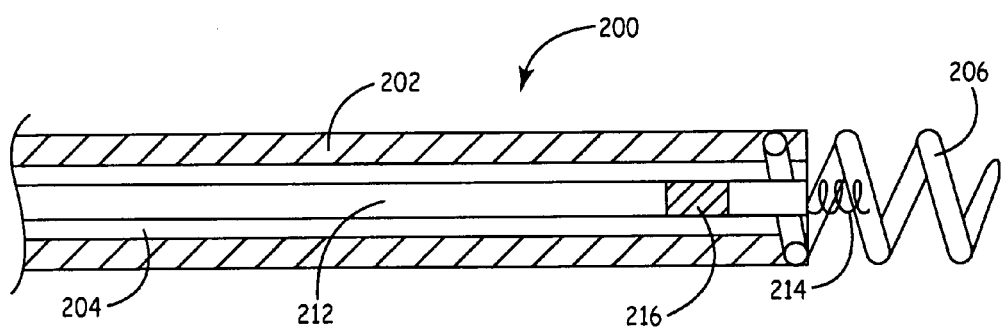
FIG. 7 is a partial side sectional view of a medical electrical lead including nanotube materials having a flexible elongated sheath removeably coupled around the lead.

FIG. 7 shows a guide catheter 200 having an elongated, tubular catheter body 202 formed as a flexible sheath having an inner lumen 204. Guide catheter 200 is provided with a fixation member 206, shown in this embodiment as a helix that allows catheter 200 to be fixed at a targeted implant site. Fixation member 206 may be a solid helix and may function exclusively as a fixation device. Alternatively, fixation member 206 may also function as an electrode and may include a nanotube coating as described herein. Lead 212 is shown as a bipolar lead having an active fixation helical tip electrode 214 at its distal end and a ring electrode 216 spaced proximally from tip electrode 214. Lead 212 may be advanced through lumen 204, such that it is removable coupled with catheter body 202. Lead 212 may then be implanted at a tissue site by advancing helical tip electrode 214 into the tissue. Guide catheter 200 may then be removed, leaving the electrode 214 implanted in the tissue. Any of the electrodes 214 and 216 and corresponding conductors extending through lead 212 may include a nanotube material as described herein. Lead 212 fabricated with conductors including a nanotube material may be formed with a very small outer dimension, for example less than 8 French and even down to approximately 1 French. The use of guide catheter 200 during implantation of lead 212 having small outer dimensions improves the handling of lead 21.

Figure 8:
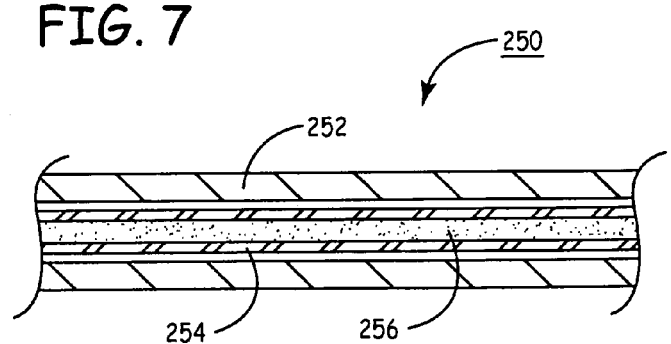
FIG. 8 is a partial side sectional view of a medical lead body according to one embodiment of the invention.

FIG. 8 is a partial side sectional view of a medical lead body according to one embodiment of the invention. Lead body 250 includes a flexible elongated conductor 256 surrounded by an insulative layer 254. Flexible elongated conductor 256 includes an electrically conductive nanotube material. As described previously, an elongated lead body structure such as flexible conductor 256 may be formed from a polymer or other resin-based material combined, encapsulated, or impregnated with nanotubes. In one embodiment, flexible elongated conductor 256 includes an elongated polymeric or resin-based structure coated or encapsulated with a nanotube composite material including a mixture of a polymer and a nanotube material. In another embodiment, flexible elongated conductor 256 is formed as an elongated structure fabricated from a composite material including a polymer and a nanotube material. In yet another embodiment, flexible elongated conductor 256 includes a porous polymeric or resin-based elongated structure impregnated with a composite material including a mixture of a nanotube material and a polymer.

An improved medical lead having carbon nanotube coated electrodes and method for manufacture provided by the present invention has been described according to specific embodiments. It is recognized that one knowledgeable in the art may conceive variations of these embodiments that generally gain the benefits provided by a carbon nanotube coated electrode. The above described embodiments should therefore not be considered limiting in regard to the following claims.

We claim:

1. In a medical device, comprising:
    a lead body;
    an elongated conductor extending through the lead body;
    at least one electrode electrically coupled to the elongated conductor;
    an electrically conductive adhesive layer on at least a portion of the at least one electrode; and
    a polymer combined with a plurality of carbon nanotubes to render the polymer conductive and electrically coupled to the electrically conductive adhesive layer, the polymer comprising one of polyurethane and silicone, wherein the plurality of carbon nanotubes comprise open ends arranged for contact with biological tissue when the at least one electrode is implanted in the body.

2. A medical device according to claim 1, wherein the at least one electrode is at least a one of the following:
    a tip electrode, a ring electrode, a defibrillation electrode, a subcutaneous electrode, a button electrode, a coil-type electrode, a helical electrode, a can electrode, a neurological stimulation electrode, a deep brain electrode, an organ electrode, a cuff electrode.

3. A medical device according to claim 1, wherein the at least one electrode comprises at least one of the following materials: a platinum material, a platinum-iridium material, a titanium material, a gold material, a tantalum material, a niobium material, a cobalt-chromium alloy material, or another electrically conductive material.

4. A medical device according to claim 1, wherein said plurality of carbon nanotubes comprises a single-wall nanotube material or a multiple-wall nanotube material.

5. A medical device according to claim 4, wherein at least a majority of said plurality of carbon nanotubes are aligned substantially normal to an adjacent portion of said electrode and in close proximity to a plurality of adjacent discrete nanotube material units.

6. A medical device according to claim 1, wherein said elongated conductor comprises an electrically conductive nanotube material.

7. A medical device according to claim 6, wherein said electrically conductive nanotube material is disposed within a relatively flexible biocompatible material.

8. A medical device according to claim 7, wherein said relatively flexible biocompatible material is electrically conductive and further comprising an electrically insulative material surrounding substantially all or the entire surface of the relatively flexible biocompatible material.

9. A medical device according to claim 6, 7 or 8, further comprising a flexible elongated sheath removeably coupled around the lead body.

10. A medical device according to claim 9, wherein said medical device has a substantially geometric lateral cross section having a dimension in the range of about 8 French units to less than about one French unit.

11. A medical device according to claim 6, further comprising at least one additional elongated conductor disposed within the relatively flexible biocompatible material and electrically insulated from the elongated electrical conductor.

12. A medical device according to claim 11, further comprising at least one of the following structures electrically coupled to the at least one additional elongated conductor: a sensor, a transducer, an electrode.

13. A medical device according to claim 12, wherein the sensor is at least a one of the following: an oxygen sensor, including without limitation, an oxygen saturation sensor, a partial pressure oxygen sensor, a blood oximetry sensor; a lactate sensor; a pH sensor; a glucose sensor; a fluid flow sensor; a temperature sensor; a pressure sensor; an optical sensor.

14. A medical device according to claim 1, further comprising a fluid material in contact with said open ends of the plurality of carbon nanotubes.

15. A medical device according to claim 14, wherein said fluid material comprises a steroid material.

16. A medical device according to claim 14, wherein said fluid material comprises an electrically conducting material.

17. A medical device according to claim 16, wherein said electrically conducting material comprises an electrically conducting solid material.

18. A medical device according to claim 17, wherein said electrically conducting solid material comprises a nanotube material.

19. A medical device according to claim 18, wherein said nanotube material is a carbon nanotube material, a boron nanotube material or a combination of carbon and boron nanotube material.

20. A medical device according to claim 17, 18, or 19, further comprising a biologically inert paste coupled to the at least one electrode.

21. A medical device, comprising:
an electrode having an exterior surface portion;
an elongated conductor extending between a proximal end and a distal end electrically coupled to said electrode; and
a polymer combined with a plurality of carbon nanotubes to render the polymer conductive and electrically connected to the exterior surface portion of the electrode, the polymer comprising one of polyurethane and silicone, wherein the plurality of carbon nanotubes comprise open ends arranged for contact with biological tissue when the at least one electrode is positioned adjacent thereto.

22. A medical device according to claim 21, wherein the elongated conductor comprises at least a one of the following a carbon nanotube material; a boron nanotube material; a material comprised of a nanotube material impregnated with an electrically conductive polymer material.

23. A medical device according to claim 21, wherein said plurality of nanotubes are disposed either in an irregular array or a substantially regular array with respect to an adjacent group of nanotubes.

24. A medical device according to claim 23, further comprising a metallic layer disposed over the exterior surface portion of the electrode and coupled to the plurality of nanotubes.

25. A medical device according to claim 24, wherein said metallic layer comprises: a platinum layer, a platinum-iridium layer, a titanium layer, a gold layer, a tantalum layer, a niobium layer, or a cobalt-chromium alloy layer.

26. A medical device according to claim 21, wherein said electrode is configured as a cardiac sense electrode, a cardiac pacing electrode, a neurological stimulation electrode, a brain stimulation electrode, an organ stimulation electrode, and/or a cardiac defibrillation electrode.

27. A medical device according to claim 21, further comprising a steroid material disposed about the open ends of at least a portion of said plurality of nanotubes.

28. A medical device according to claim 21, further comprising an electrically conductive paste coupled to at least a portion of said plurality of nanotubes.

29. A method for manufacturing a medical electrode having an electrode surface adapted for electrical communication with biological tissue, wherein the method comprises:
providing an electrically conductive adhesive layer on at least a portion of the electrode surface;
forming a polymer combined with a plurality of carbon nanotubes to render the polymer conductive and electrically coupled to the electrically conductive adhesive layer, the polymer comprising one of polyurethane and silicone, wherein the plurality of carbon nanotubes comprise open ends arranged for contact with the biological tissue when the medical electrode is positioned adjacent thereto.

30. A method according to claim 29, wherein the electrode surface comprises a platinum material, a platinum-iridium material, a titanium material, a gold material, a tantalum material, or a cobalt-chromium alloy material.

31. A method according to claim 29, wherein said medical electrode is a distal end portion of a helical coil and further comprising the steps of:
spreading the coil at said distal end portion to form a helical screw portion so that the helix can perform as an active fixation lead.

32. A method according to claim 29, wherein during the forming of the polymer combined with the plurality of carbon nanotubes, performing the following sub-step:
applying an alternating-current or direct-current electric field to orient the plurality of carbon nanotubes relative to the electrode surface.

33. A method according to claim 29, wherein the medical electrode structure is formed with a hollow portion for conveying a fluid or paste to said biological tissue.

34. A method according to claim 33, further comprising the step of:
mechanically coupling an elongated medical electrical lead to said electrode, wherein said lead has a fluid conduit formed therein and said fluid conduit is in fluid communication with said hollow portion and wherein an electrical conductor disposed within said lead is in electrical communication with said medical electrode.

* * * * *